United States Patent [19]

Fontana

[11] Patent Number: 5,462,950
[45] Date of Patent: Oct. 31, 1995

[54] METHODS OF TREATING MENSTRUAL SYMPTOMS AND COMPOSITIONS THEREFORE

[75] Inventor: Steven A. Fontana, Martinsville, Ind.

[73] Assignee: Eli Lilly and Company, Indianapolis, Ind.

[21] Appl. No.: 171,392

[22] Filed: Dec. 21, 1993

[51] Int. Cl.$^6$ .................. A61K 31/445; A61K 31/40; A61K 31/38
[52] U.S. Cl. .................. 514/324; 514/422; 514/443
[58] Field of Search .................................. 514/324, 422

[56] References Cited

U.S. PATENT DOCUMENTS

| | | | |
|---|---|---|---|
| 4,133,814 | 1/1979 | Jones et al. | 260/326.55 A |
| 4,380,635 | 4/1983 | Peters | 546/202 |
| 4,418,068 | 11/1983 | Jones | 424/267 |
| 4,888,343 | 12/1989 | Jones et al. | 514/264 |
| 5,075,321 | 12/1991 | Schreiber . | |

FOREIGN PATENT DOCUMENTS

| | | |
|---|---|---|
| WO93/10113 | 5/1993 | Japan . |
| WO92/05786 | 4/1992 | WIPO . |
| WO93/1074 | 6/1993 | WIPO . |

OTHER PUBLICATIONS

Draper et al., "Effects of Ralozifene (LY139481 HCl) on Biochemical Markers of Bone and Lipid Metabolism in Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am. Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Min. Res., Tampa, Sep. 18–22, 1993.

Glasebrook et al., "Multiple Binding Sites for the Anti–estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti–Estrogen, Simulates the Effects of Estrogen in Inhibiting Bone Resorption Through Regulating TGFB–3 Expression in Bone; " .Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109:1981, 987–989.

Black, L. J. "Biological Actions and Binding Properties of a New Estrogen Antagosist LY117018," In: Homone Antagonists, 129–182, 1982 (M. K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy (List continued on next page.)

*Primary Examiner*—Zohreh Fay
*Attorney, Agent, or Firm*—Steven A. Fontana; David E. Boone

[57] ABSTRACT

The present invention provides a method of alleviating one or more menstrual symptoms in a woman comprising administering to said woman in need of treatment an effective amount of a compound having the formula

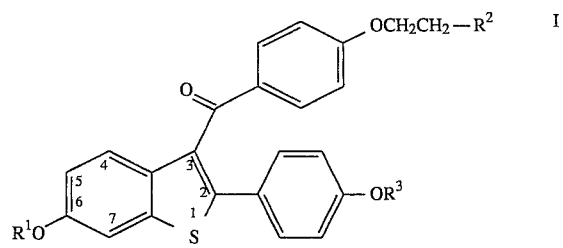

wherein $R^1$ and $R^3$ are independently hydrogen, —$CH_3$, —CO—($C_1$–$C_6$ alkyl), or —CO—Ar in which Ar is optionally substituted phenyl; and $R^2$ is selected from the group consisting of pyrrolidino, hexamethyleneimino and piperidino; or a pharmaceutically acceptable salt or solvate thereof.

The present invention also provides the aforementioned method and further comprises administering to said woman an effective amount of at least one pharmaceutical agent selected from the group consisting of an analgesic, a diuretic, and an antihistamine, and compositions therefore.

12 Claims, No Drawings

OTHER PUBLICATIONS of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl) ethoxyl]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl] melthanone Hydrochloride (LY156758), a Remarkably Effective Estrogen Antagonist with Only Minimal Intrinsic Estrogenicity, J. Med. Chem. 27(8), 1984, 1057–1066.

Penland, J. G., et al., "Dietary Calcium and Manganese Effects on Menstrual Cycle Symptoms", Am. J. Obstet, Gynecol., 168(5):1417–1423 (1993).

METHODS OF TREATING MENSTRUAL SYMPTOMS AND COMPOSITIONS THEREFORE

BACKGROUND OF THE INVENTION

In women, the normal menstrual cycle is characterized by numerous neuroendocrine and physiologic changes. In addition to hormonal variations, body weight and basal metabolic rate increase during the luteal phase, and reliable although complex differences among cycle phases have been found in brain electrical activity and sensory function. However, clinical observation and controlled studies continue to find that psychologic and behavioral disturbances are among the most prevalent symptoms reported by women with menstrual disorders.

Psychologic and behavioral symptoms which have been suggested to occur during menstruation include, for example, poorer work or school performance, increased napping and time in bed, increased time at home, avoiding social activities, decreased efficiency, insomnia, forgetfulness, confusion, poorer judgement, difficulty concentrating, distractibility, increased accidents, poorer motor coordination, crying, loneliness, anxiety, restlessness, irritability, mood swings, depression, and tension. The effect of these symptoms can be compounded by physical menstrual symptoms such as, for example, dizziness, faintness, cold sweats, nausea, vomiting, hot flashes, muscle stiffness, headache, cramps, backache, fatigue, general aches and pains, and water retention including, for example, weight gain, skin disorders, painful breasts, and swelling. [See, e.g., Penland, J. G., et al., *Am. J. Obstet. Gynecol.* 168 (5) :1417–1423 (1993)] . Collectively, these and other known symptoms of menstruation are herein referred to as menstrual symptoms.

Numerous treatments have been suggested for alleviating or minimizing menstrual symptoms. These include, for example, variation in total energy intake and consumption of protein, fat, carbohydrates, vitamins B and E, magnesium, zinc, calcium, manganese, and fatty acids, such as linolenic acid (primrose oil) [see, e.g., Penland, J. G., et al. supra]. Other treatments include the administration of an analgesic/anti-inflammatory agent such as ibuprofen in combination with a diuretic agent and, optionally, an antihistamine such as pyrilamine maleate (see, e.g. U.S. Pat. No. 4,888,343).

Although these and other treatments are available, a multitude of women continue to suffer one or more menstrual symptoms on a monthly basis. Accordingly, the present invention provides methods for alleviating one or more menstrual symptoms in women, and compositions therefore.

SUMMARY OF THE INVENTION

One aspect of the present invention provides a method of alleviating one or more menstrual symptoms in a woman comprising administering to said woman in need of treatment an effective amount of a compound having the formula

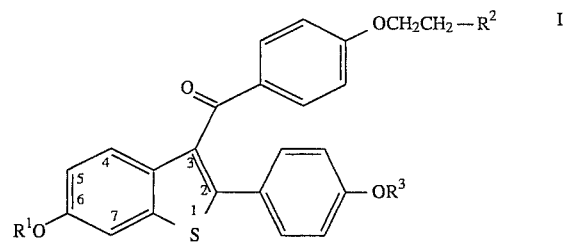

wherein $R^1$ and $R^3$ are independently hydrogen, —$CH_3$, —CO—($C_1$-$C_6$ alkyl), or —CO—Ar in which Ar is optionally substituted phenyl; and $R^2$ is selected from the group consisting of pyrrolidino, hexamethyleneimino and piperidino; or a pharmaceutically acceptable salt or solvant thereof.

Another aspect of the present invention provides the aforementioned method and further comprises administering to said woman an effective amount of at least one pharmaceutical agent selected from the group consisting of an analgesic, a diuretic, and an antihistamine, and pharmaceutical compositions therefore. As used herein, the term "pharmaceutical agent" refers to an analgesic, a diuretic, and/or an antihistamine.

DETAILED DESCRIPTION OF THE INVENTION

The present invention concerns the discovery that a select group of 2-phenyl-3-aroylbenzothiophenes (benzothiophenes), those of formula I, are useful for effectively alleviating one or more menstrual symptoms in women. Thus, the present invention provides a method of effectively alleviating one or more menstrual symptoms in women comprising administering to a women in need of treatment an effective amount of a compound of formula I, or a pharmaceutically acceptable salt or solvate thereof.

The term "alleviating" is defined to include prophylactically treating a woman from incurring one or more menstrual symptoms, holding in check such symptoms, and/or treating existing symptoms. As such, the present method includes both medical therapeutic and/or prophylactic treatment, as appropriate.

Raloxifene, the hydrochloride salt of a compound of formula I in which $R^1$ and $R^3$ each are hydrogen, and $R^2$ is 1-piperidinyl, is a nuclear regulatory molecule. Raloxifene has been shown to bind to estrogen receptors and originally was thought to have antiestrogenic activity because it blocked the ability of estrogen to activate uterine tissue and estrogen dependent breast cancers. Indeed, raloxifene does block the action of estrogen in some cells; however in other cell types, raloxifene activates the same genes as estrogen activates and displays the same pharmacology, e.g., osteoporosis, hyperlipidemia. As a result, raloxifene has been referred to as an antiestrogen with mixed agonist-antagonist properties.

Although raloxifene and estrogen generally utilize and compete for the same receptors, the pharmacological outcome of administration of the two agents is not easily predicted, and is distinct to each.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

Compounds of formula I can be made according to established procedures, such as those detailed in U.S. Pat. Nos. 4,133,814, 4,418,068, and 4,380,635, each of which is herein incorporated by reference. The term "substituted phenyl" refers to a phenyl molecule having one or two substituents selected from the group consisting of $C_1$–$C_4$ alkyl, $C_1$–$C_5$ alkoxy, hydroxy, nitro, chloro, fluoro, or tri(chloro or fluoro)methyl. The terms "$C_1$–$C_4$ alkyl" and "$C_1$–$C_5$ alkoxy" have the definitions as stated in the above-incorporated U.S. patents.

The compounds used in the methods of this invention form pharmaceutically acceptable acid and base addition salts with a wide variety of organic and inorganic acids and bases, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, b-hydroxybutyrate, butyne- 1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts and solvates generally have enhanced solubility characteristics compared to the compound from which they are derived, and thus are often more amenable to formulation as liquids or emulsions.

Pharmaceutical formulations can be prepared by procedures known in the art. For example, the compounds of formula I can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Whether administered alone or in combination with the aforementioned pharmaceutical agents, the particular dose of a compound of formula I required to inhibit menstrual symptoms according to this invention will depend upon the severity of the condition, the route of administration, and related factors that will be decided by the attending physician. Generally, accepted and effective daily doses will be from about 0.1 mg to about 1000 mg/day, and more typically from about 50 mg to about 600 mg/day. Such doses will be administered to a subject in need of treatment from once to about three times each day, or more often as needed to effectively treat one or more of the symptoms.

It is usually preferred to administer a compound of formula I in the form of an acid addition salt, as is customary in the administration of pharmaceuticals bearing a basic group such as the piperidino ring. It is also advantageous to administer such a compound by the oral route.

In addition to the above-described method, the present invention further provides a method for alleviating one or more menstrual symptoms in women comprising administering to said woman in need of treatment an effective amount of a compound of formula I, and further comprises administering to said woman an effective amount of at least one pharmaceutical agent selected from the group consisting of an analgesic, a diuretic, and an antihistamine.

The term "analgesic" refers to known pharmaceutical compounds having analgesic activity such as, for example, acetylsalicylic acid (aspirin), acetominophen, ibuprofen, and the like. Of these, ibuprofen and acetylsalicylic acid are preferred because each also has anti-inflammatory activity. Generally, the amount of analgesic administered will be that which is known in the art. For example, ibuprofen will be administered at a daily dosage range from about 100 mg to about 2 gm, and preferably in the range from about 200 mg to about 800 mg. However, the average daily dose of aspirin will be in the range from about 200 mg to about 5 gm, preferably from about 500 mg to about 2 gm.

The term "diuretic" encompasses known compounds such as the benzothiadiazides, such as, for example, chlorothiazide, hydrochlorothiazide, benzthiazide, and the like, acetazolamide and its analogs, ethacrynic acid, furosemide, bumetanide, amiloride, thriamterene, a xanthine, a combination compound such as pamabrom, and the like. Of these, hydrochlorothiazide and pamabrom are preferred. The amount of diuretic useful in the practice of the present invention is diuretic specific and will vary from about 2 mg to about 50 mg. More particularly, hydrochlorothiazide is administered at an average daily dose from about 5 mg to about 250 mg, and pamabrom's average daily dose is from about 5 mg to about 500 mg. For both compounds, the preferred range is from about 25 mg to about 200 mg.

The term "antihistamine" encompasses known compounds, such as, for example, ethanolamines, (diphenhydramine, carbinoxamine, and the like), ethylenediamines (tripelennamine and pyrilamine), alkylamines (chloropheniramine, triprolidine, and the like), phenothiazines (promethazine, trimeprazine, and the like), and piperidines (cyproheptadiene, azatadine, and the like), and the like. Preferred antihistamines are those which have sedative/calming effects, and an especially preferred antihistamine is pyrilamine or a pharmaceutically acceptable salt thereof. When an antihistamine is employed in the practice of this invention, the average daily dose will be in the range from about 12 mg to about 400 mg. When using the preferred antihistamine, pyrilamine (or any of its pharmaceutically acceptable salts, particularly pyrilamine maleate), the average daily dose will be from about 125 mg to about 400 mg.

Methods for preparing formulations of the aforementioned pharmaceutical agents, either as independent agents or in various combinations, as well as methods of administration, are well known in the art (see, e.g., U.S. Pat. No. 4,888,343).

Compounds of formula I, alone or in combination with the pharmaceutical agents used in the methods of the present invention, are administered to premenopausal women for about 5 to about 10 days each month. Administration of formula I compounds, with or without the pharmaceutical agents of the present invention, will commence on the first day of menstruation and will terminate on the last day of menstruation. For most women, the methods of the present invention will be carried out for 5 to 7 days.

The present invention further provides a pharmaceutical composition for alleviating one or more menstrual symptoms in women comprising a compound of formula I and at least one pharmaceutical agent selected from the group consisting of an analgesic, a diuretic, and an antihistamine, in combination with a pharmaceutically acceptable carrier, diluent or excipient.

Compositions of the present invention which provide the aforementioned daily dose of each active ingredient are prepared by known methods, particularly those procedures described above for the preparation of pharmaceutical formulations of compounds of formula I.

Compounds of formula I, alone or in combination with a pharmaceutical agent of the present invention, generally will be administered in a convenient formulation. The following formulation examples only are illustrative and are not intended to limit the scope of the present invention.

FORMULATIONS

In the formulations which follow, "active ingredient" means a compound of formula I.

Formulation 1

Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

Formulation 2

Raloxifene Capsule

| Ingredient | Quantity (mg/capsule) |
| --- | --- |
| Raloxifene HCl | 1 |
| Starch, NF | 112 |
| Starch flowable powder | 225.3 |
| Silicone fluid 350 centistokes | 1.7 |

Formulation 3

Raloxifene Capsule

| Ingredient | Quantity (mg/capsule) |
| --- | --- |
| Raloxifene HCl | 5 |
| Starch, NF | 108 |
| Starch flowable powder | 225.3 |
| Silicone fluid 350 centistokes | 1.7 |

Formulation 4

Raloxifene Capsule

| Ingredient | Quantity (mg/capsule) |
| --- | --- |
| Raloxifene HCl | 10 |
| Starch, NF | 103 |
| Starch flowable powder | 225.3 |
| Silicone fluid 350 centistokes | 1.7 |

Formulation 5

Raloxifene Capsule

| Ingredient | Quantity (mg/capsule) |
| --- | --- |
| Raloxifene HCl | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6

Tablets

| Ingredient | Quantity (mg/tablet) |
|---|---|
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.1–1000 mg of active ingredient are made up as follows:

Formulation 7

Tablets

| Ingredient | Quantity (mg/tablet) |
|---|---|
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 8

Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Formulation 9

Raloxifene, Ibuprofen, Pamabrom, and Pyrilamine Maleate Capsule

| Ingredient | Quantity (mg/capsule) |
|---|---|
| Raloxifene HCl | 50 |
| Ibuprofen | 150 |
| Pamabrom | 25 |
| Pyrilamine Maleate | 15 |
| Avicel pH 101 | 50 |
| Starch 1500 | 117.50 |
| Silicon Oil | 2 |
| Tween 80 | 0.50 |
| Cab-O-Sil | 0.25 |

Formulation 10

Raloxifene, Ibuprofen, and Pamabrom Capsule

| Ingredient | Quantity (mg/capsule) |
|---|---|
| Raloxifene HCl | 50 |
| Ibuprofen | 150 |
| Pamabrom | 25 |
| Avicel pH 101 | 82.50 |
| Starch 1500 | 90 |
| Silicon Oil | 2 |
| Tween 80 | 0.50 |

Formulation 11

Raloxifene, Ibuprofen, and Hydrochlorothiazide Capsule

| Ingredient | Quantity (mg/capsule) |
|---|---|
| Raloxifene HCl | 50 |
| Ibuprofen | 200 |
| Hydrochlorothiazide HCl | 12.50 |
| Starch 1500 | 134.50 |
| Silicon Oil | 2 |
| Tween 80 | 0.50 |
| Cab-O-Sil | 0.25 |

Formulation 12

Raloxifene, Ibuprofen, and Hydrochlorothiazide Tablet

| Ingredient | Quantity (mg/capsule) |
|---|---|
| Raloxifene HCl | 50 |
| Ibuprofen | 200 |
| Hydrochlorothiazide HCl, USP | 12.50 |
| Corn Starch NF | 50 |

-continued

| Ingredient | Quantity (mg/capsule) |
|---|---|
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

Test Procedure

Three to fifty women are selected for the clinical study. The women have regular menses, are in good general health, and suffer from one or more of the above mentioned PMS/LPDD symptoms. Because of the somewhat idiosyncratic and subjective nature of these symptoms, the study has a placebo control group, i.e., the women are divided into two groups, one of which receives the active agent of this invention and the other receives a placebo. Women in the test group receive between 50–600 mg of the drug per day by the oral route. They continue this therapy for 1–3 months. Accurate records are kept as to the number and severity of the symptoms in both groups and at the end of the study these results are compared. The results are compared both between members of each group and also the results for each patient are compared to the symptoms reported by each patient before the study-began.

Utility of compounds of the present invention, including compounds of formula I used alone or in combination with the pharmaceutical agents described herein, is illustrated by the positive impact they have on one or more menstrual symptoms when used in a study as above.

I claim:

1. A method of alleviating one or more physical menstrual symptoms selected from the group consisting of dizziness, faintness, cold sweats, nausea, vomiting, hot flashes, muscle stiffness, headache, cramps, backache, fatigue, general aches, and pains, and water retention-related weight gain, skin disorders, painful breasts, and swelling in a woman comprising administering to said woman in need of treatment an effective amount of a compound having the formula

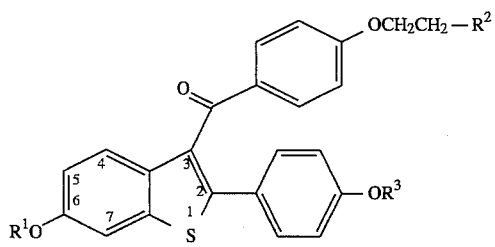

wherein $R^1$ and $R^3$ are independently hydrogen, —$CH_3$, —CO—($C_1$–$C_6$ alkyl), or —CO—Ar in which Ar is optionally substituted phenyl; and $R^2$ is selected from the group consisting of pyrrolidino, hexamethyleneimino and piperidino; or a pharmaceutically acceptable salt or solvent thereof.

2. The method of claim 1 wherein said compound is the hydrochloride salt thereof.

3. The method of claim 1 wherein said compound is

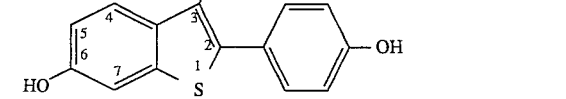

or its hydrochloride salt.

4. The method of claim 1 which further comprises administering to said woman an effective amount of at least one pharmaceutical agent selected from the group consisting of an analgesic, a diuretic, and an antihistamine.

5. The method of claim 4 wherein said compound is the hydrochloride salt thereof.

6. The method of claim 5 wherein said compound is

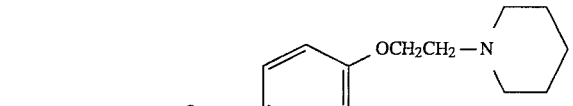

or its hydrochloride salt.

7. The method of claim 6 wherein said pharmaceutical agent is an analgesic.

8. The method of claim 6 wherein said pharmaceutical agent is a diuretic.

9. The method of claim 6 wherein said pharmaceutical agent is an antihistamine.

10. The method of claim 6 wherein said pharmaceutical agents are an antihistamine and an analgesic.

11. The method of claim 6 wherein said pharmaceutical agents are an antihistamine and a diuretic.

12. The method of claim 6 wherein said pharmaceutical agents are an analgesic and a diuretic.

* * * * *